(12) United States Patent
Wondka

(10) Patent No.: US 8,082,921 B2
(45) Date of Patent: Dec. 27, 2011

(54) METHODS, SYSTEMS AND DEVICES FOR DESUFFLATING A LUNG AREA

(76) Inventor: Anthony David Wondka, Westlake Village, CA (US)

(*) Notice: Subject to any disclaimer, the term of this patent is extended or adjusted under 35 U.S.C. 154(b) by 2174 days.

(21) Appl. No.: 10/831,573

(22) Filed: Apr. 24, 2004

(65) Prior Publication Data

US 2005/0022809 A1 Feb. 3, 2005

Related U.S. Application Data

(60) Provisional application No. 60/465,028, filed on Apr. 25, 2003.

(51) Int. Cl.
*A61M 11/00* (2006.01)

(52) U.S. Cl. ......... 128/203.12; 128/207.14; 128/207.15; 604/509; 604/516

(58) Field of Classification Search ............. 128/203.12, 128/203.25, 207.14, 207.15; 604/509, 516
See application file for complete search history.

(56) References Cited

U.S. PATENT DOCUMENTS

| | | | | | |
|---|---|---|---|---|---|
| 5,706,830 | A | * | 1/1998 | Parker | 128/203.12 |
| 6,287,290 | B1 | * | 9/2001 | Perkins et al. | 604/516 |
| 6,308,703 | B1 | * | 10/2001 | Alving et al. | 128/203.12 |
| 6,527,761 | B1 | * | 3/2003 | Soltesz et al. | 604/516 |
| 6,682,520 | B2 | * | 1/2004 | Ingenito | 604/514 |
| 7,165,548 | B2 | * | 1/2007 | Deem et al. | 128/207.16 |
| 7,186,259 | B2 | * | 3/2007 | Perkins et al. | 606/108 |

* cited by examiner

*Primary Examiner* — Steven Douglas

(57) ABSTRACT

Methods, systems and devices are described for temporarily or permanently evacuating stagnating air from a diseased lung area, typically for the purpose of treating COPD. Evacuation is accomplished by displacing the stagnant $CO_2$-rich air with a readily diffusible gas using a transluminal indwelling catheter specially configured to remain anchored in the targeted area for long term treatment without supervision. Appropriate elevated positive gas pressure in the targeted area is then regulated via the catheter and a pneumatic control unit to force under positive pressure effusion of the diffusible gas out of the area into neighboring areas while inhibiting infusion of other gases thus effecting a gradual gas volume decrease and deflation of the targeted area.

48 Claims, 10 Drawing Sheets

DETAIL A

DETAIL B

DETAIL C

DETAIL D

FIGURE 2 _Desufflation Gas Flux Schematic Model_

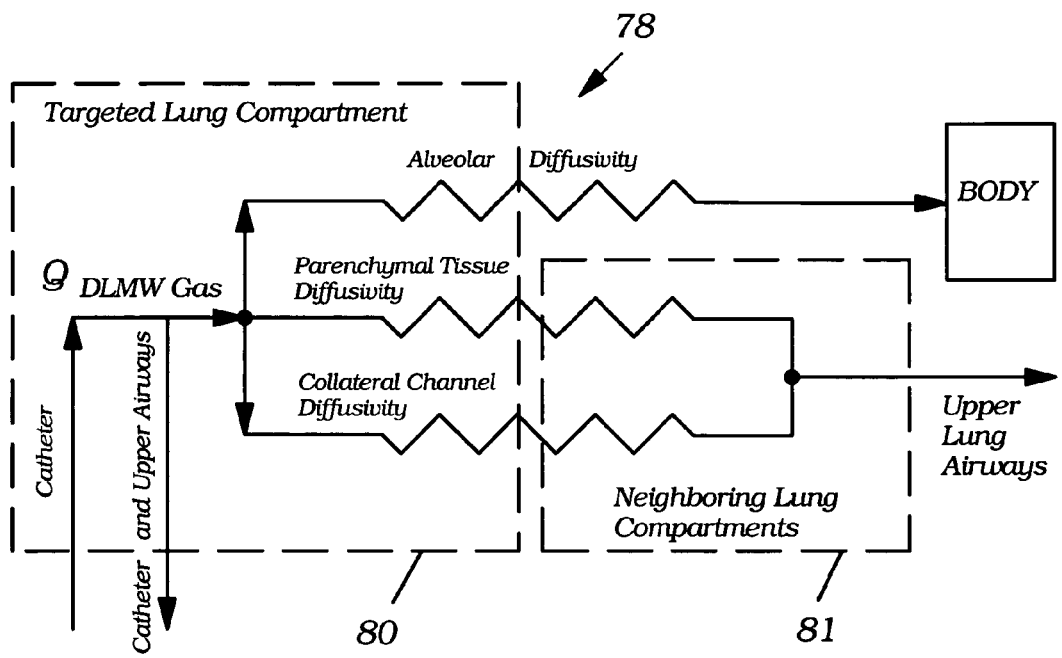

_Desufflation Mathematical Model_

$J_{total, tla} = J_{HeO2(alv)} + J_{HeO2(lp)} + J_{HeO2(cc)} + Q_{HeO2(ua)} - Q_{HeO2(C)}$ J= Molar Gas Volume Flux; Q= Gas Flow; tla= targeted lung area; alv = alveolar surface; lp = lung parenchymal surface; cc = collateral channels; ua = upper airways; C = catheter; $HeO_2$ = Helium-Oxide diffusible low mol. wt. (DLMW) gas.

$J = D(\alpha \Delta P + \beta \Delta C)$; $D \propto (K * A)/L$; $K \propto \rho/\nu$ D = diffusion Coeficient; $\Delta P$ = pressure gradient; $\Delta C$ = concentration gradient; A = surface area; L = tissue thickness; $\rho$ = gas density; $\nu$ = gas kinematic viscosity; $\alpha$, $\beta$, K = tissue-specific constants.

FIGURE 3
Gas Wash Out Stage　　　　　　　Deflation Stage
FIG. 3A  Diffusible LMW Gas Delivery
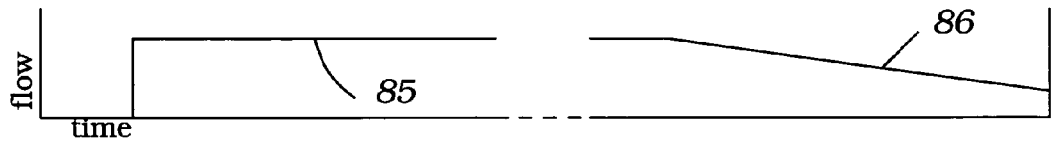
FIG. 3B  Diffusible LMW Gas Delivery
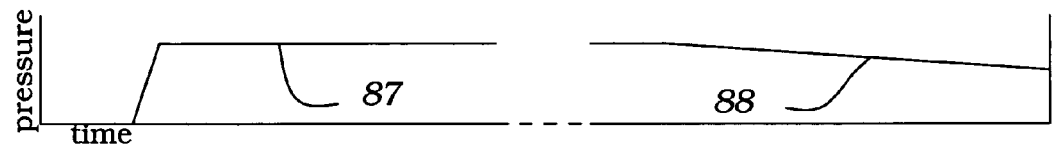
FIG. 3C Targeted Area Pressure and Neighboring Lung Area Pressure
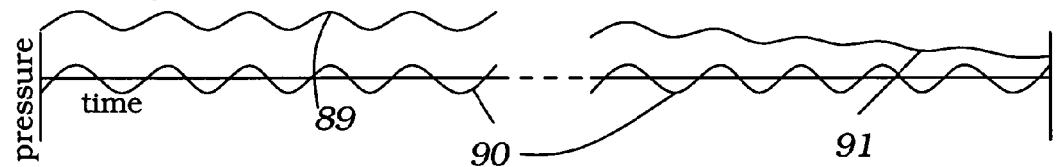
FIG. 3D  Gas Concentration
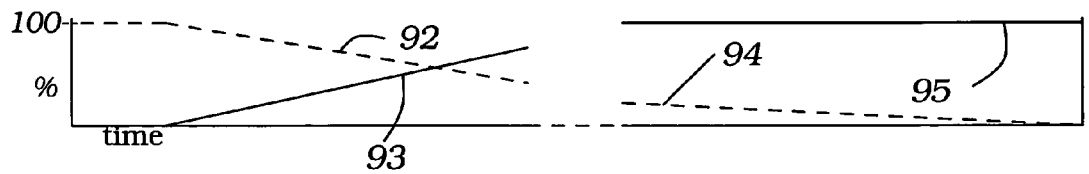
FIG. 3E  Targeted Area Gas Volume
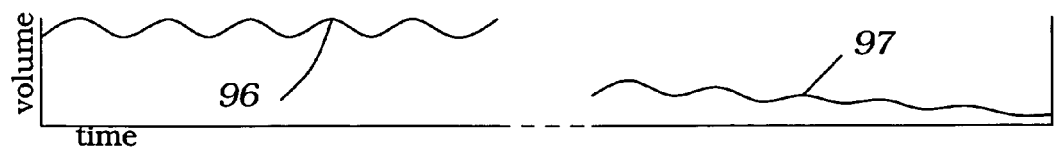

FIGURE 4   DESUFFLATION GAS PROFILES

FIG. 5A
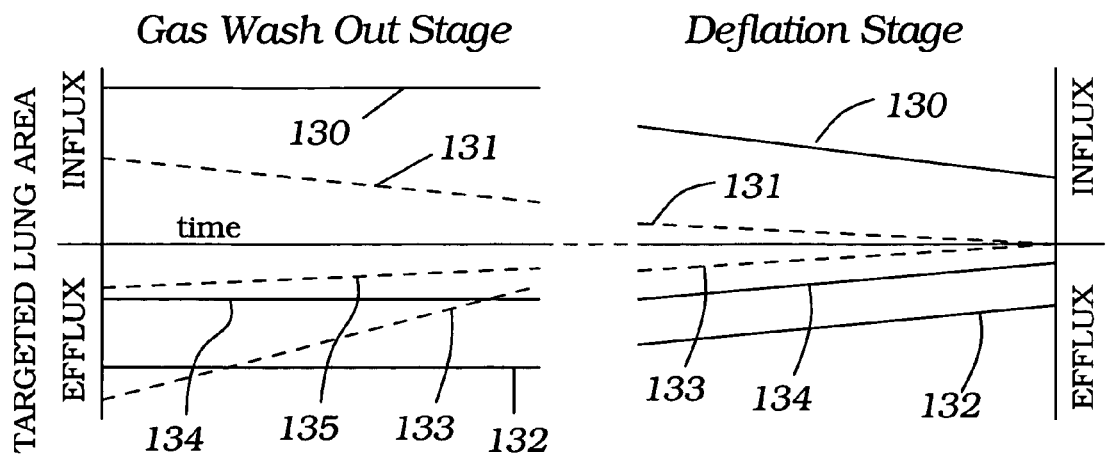
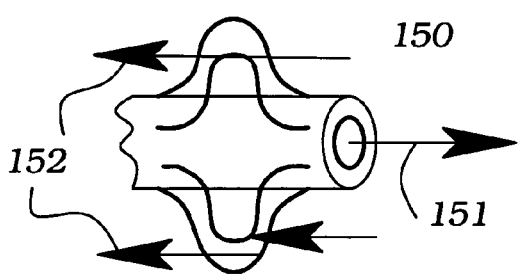
FIG. 5B
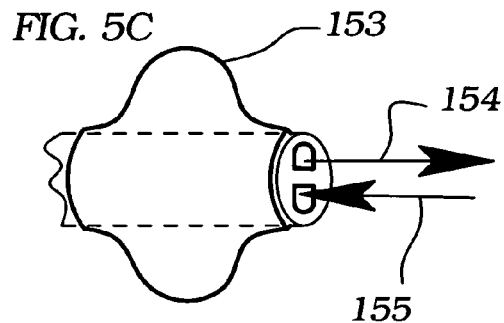
FIG. 5C
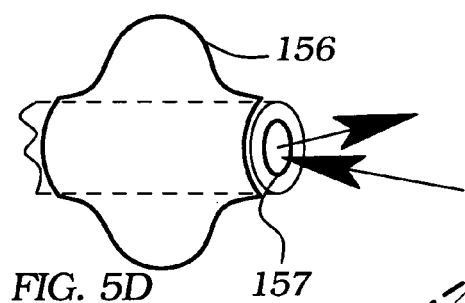
FIG. 5D
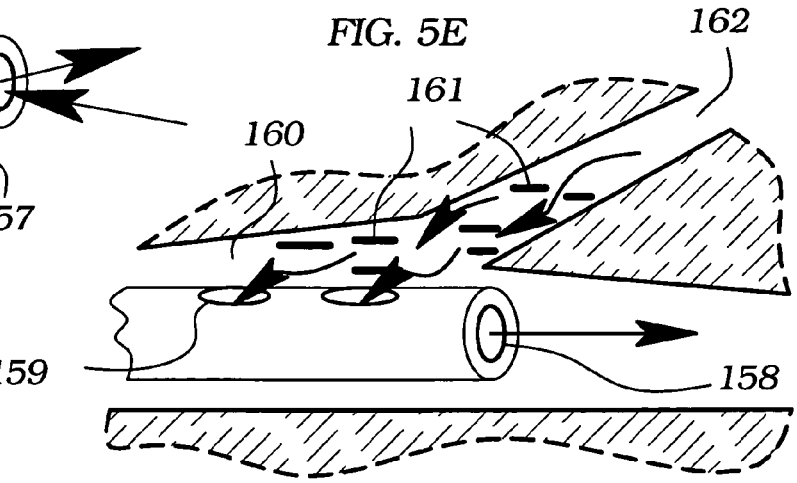
FIG. 5E

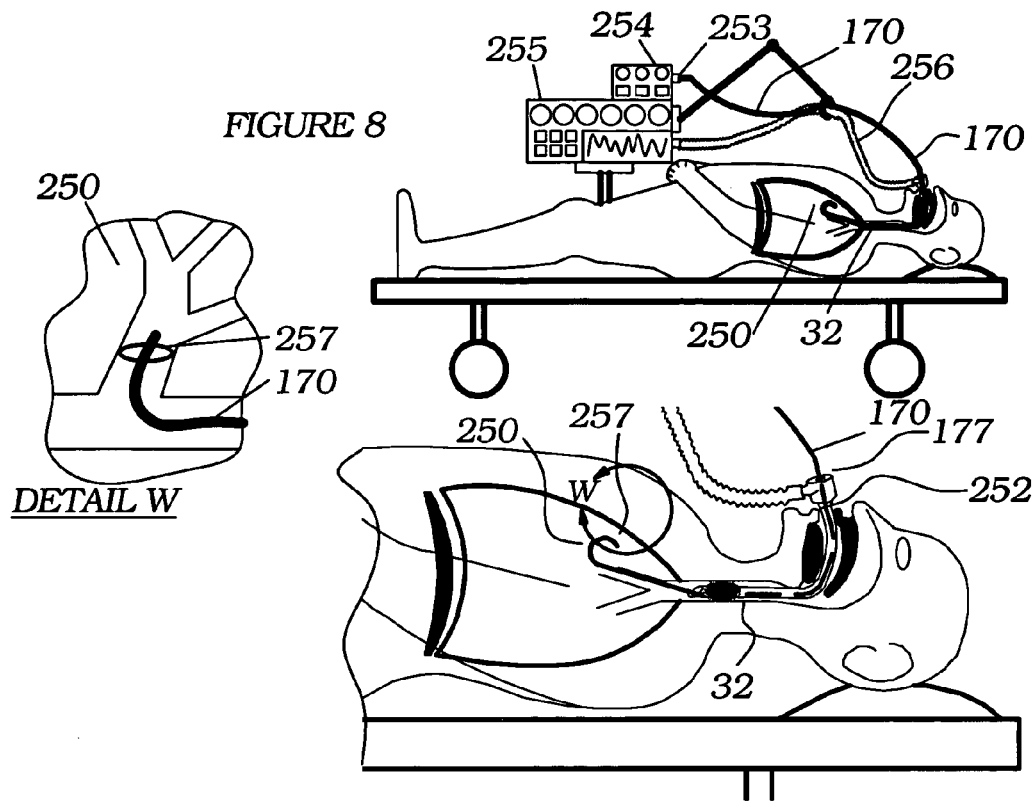
FIGURE 8
DETAIL W
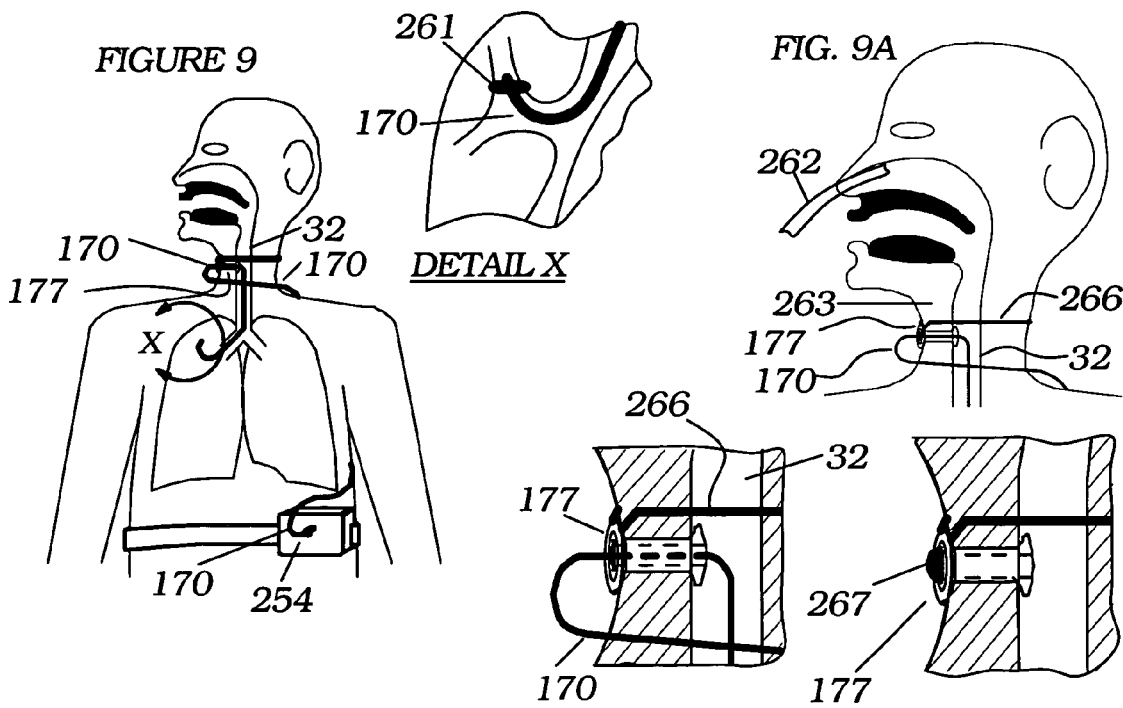
FIGURE 9
DETAIL X
FIG. 9A

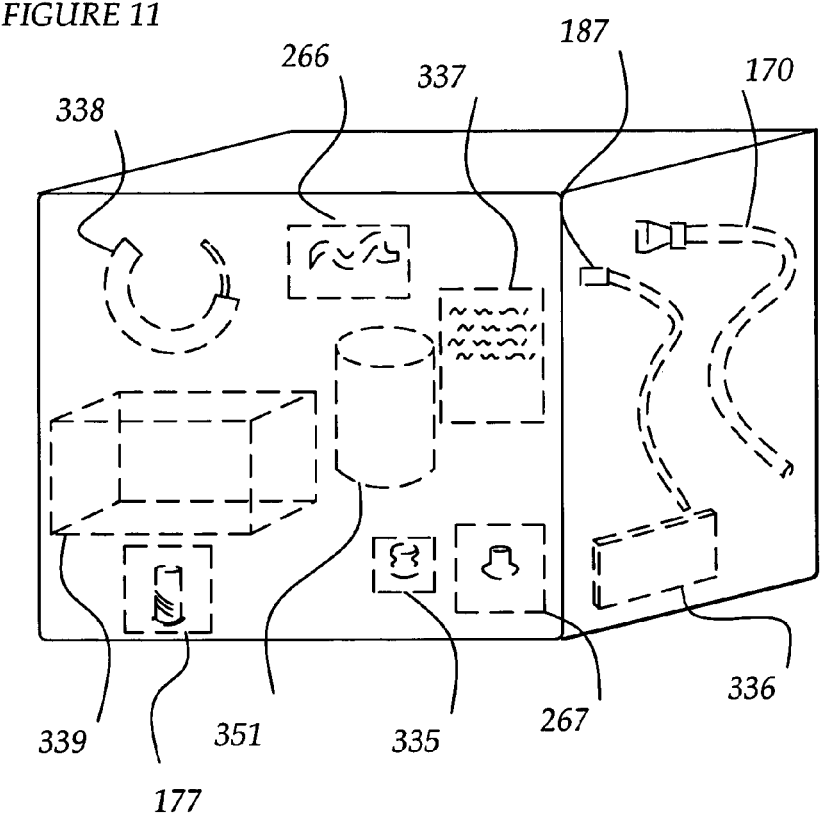

METHODS, SYSTEMS AND DEVICES FOR DESUFFLATING A LUNG AREA

CROSS REFERENCE TO RELATED APPLICATIONS

This application claims Provisional Patent Application No. 60/465,028 as a predicate application with the respective priority date of Apr. 25, 2003.

STATEMENT REGARDING FEDERALLY SPONSORED RESEARCH OR DEVELOPMENT

Not Applicable

DESCRIPTION OF ATTACHED APPENDIX

Not Applicable

GOVERNMENT INVENTION OR CONTRACT WITH GOVERNMENT

None
Entity: Small Entity Concern
Prior Art:
U.S. Patents and Patent Applications: 5,972,026; 6,083,255; 6,174,323; 6,488,673; 6,514,290; 6,287,290; 6,527,761; 6,258,100; 6,293,951; 6,328,689; 6,402,754; US2002/0042564; US2002/0042565; US2002/0111620; US2001/0051799; US2002/0165618;

Foreign patents and patent applications: EP1078601; WO98/44854; WO99/01076; WO99/32040; WO99/34741; WO99/64109; WO0051510; WO00/62699; WO01/03642; WO01/10314; WO01/13839; WO01/13908 WO01/66190.

Other Related Publications:
Fink J.B.; *Helium-oxygen: An Old Therapy Creates New Interest*. J Resp Care Pract Apr 1999; 71-76
Christopher KL et al.; *Transtracheal oxygen for refractory hypoxemia*. JAMA 1986; 256: 494-7
Gaebek J.B. et al; *Efficacy of Selective Intrabronchial Air Insufflation in Acute Lobar Collapse*. Am J of Sur 1992; 164:501-505
Fishman A. et al; *Patients at High Risk of Death after Lung-Volume-Reduction Surgery*. NEJM 2001; 15:1075-1083
Fessler H.E.; Collateral ventilation, the bane of bronchoscopic volume reduction. Am J Resp Crit Care Med. 2005 Mar. 1; 171(5): 423-4
Venuta F et al.: *Bronchoscopic lung-volume reduction with one-way valves in patients with heterogenous emphysema;* Ann Thorac Surg., 2005 Feb: 79(2):411-7.

BACKGROUND OF THE INVENTION

The present invention relates to the field of respiratory therapy and specifically to the field of treating Chronic Obstructive Pulmonary Disease (COPD).

COPD is a worldwide problem of high prevalence, effecting tens of millions of people and is one of the top five leading causes of death. COPD is a spectrum of problems, including bronchitis and emphysema, and involves airway obstruction, tissue elasticity loss and trapping of stagnant $CO_2$-rich air in the lung. There are two basic origins of emphysema; a lesser common origin stemming from a genetic deficiency of $alpha_1$-antitripsin and a more common origin caused by toxins from smoking or other environment sources. In both forms there is a breakdown in the elasticity in the functional units, or lobules, of the lung changing clusters of individual alveoli into large air pockets, thereby significantly reducing the surface area for gas transfer. In some cases air leaks out of the frail lobules to the periphery of the lung causing the lung's membranous lining to separate from the parenchymal tissue to form large air vesicles called bullae. The elasticity loss also causes small airways to become flaccid tending to collapse during exhalation, trapping large volumes of air in the now enlarged air pockets, thus reducing bulk air flow exchange and causing $CO_2$ retention in the trapped air. Mechanically, because of the large amount of trapped air in the lung at the end of exhalation, known as elevated residual volume, the intercostal and diaphragmatic inspiratory muscles are forced into a pre-loaded condition, reducing their leverage at the onset of an inspiratory effort thus increasing work-of-breathing and causing dyspnea. In emphysema therefore more effort is expended to inspire less air and the air that is inspired contributes less to gas exchange.

Conventionally prescribed therapies for emphysema and other forms of COPD include pharmacological agents such as aerosolized bronchodilators and anti-inflammatories; long term oxygen therapy (LTOT); respiratory muscle rehabilitation; pulmonary hygiene such as lavage or percussion therapy; continuous positive airway pressure (CPAP) via nasal mask; trans-tracheal oxygen therapy (TTOT) via tracheotomy. These therapies all have certain disadvantages and limitations with regard to effectiveness because they do not address, treat or improve the debilitating elevated residual volume in the lung. After progressive decline in lung function despite attempts at conventional therapy, patients may require mechanical ventilation.

Newer mechanical ventilation techniques to address COPD is well reported in the literature and include HeliOx ventilation, Nitric Oxide ventilation, liquid ventilation, high frequency jet ventilation, and tracheal gas insufflation. Because these modes do nothing to address, treat or improve the hyperinflated residual volume of the COPD or emphysema patient, and because mechanical ventilation is performed on the lung as a whole and inherently can not target a specific lung area that might be more in need of treatment, mechanical ventilation is an ineffective solutions.

There have been significant efforts to discover new treatments such as treatment with substances that protect the elastic fibers of the lung tissue. This approach may slow the progression of the disease by blocking continued elastin destruction, but a successful treatment is many years away, if ever. It may be possible to treat or even prevent emphysema using biotechnology approaches such as monoclonal antibodies, stem cell therapy, viral therapy, cloning, or xenographs however, these approaches are in very early stages of research, and will take many years before their viability is even known.

In order to satisfy the more immediate need for a better therapy a surgical approach called lung volume reduction surgery (LVRS) has been extensively studied and proposed by many as a standard of therapy. This surgery involves surgically resecting some of the diseased hyperinflated lung tissue, usually the lung's apical sections, thus reducing residual volume and improving the patient's breathing mechanics and possibly gas exchange. Approximately 9000 people have undergone LVRS, however the results are not always favorable. There is a high complication rate of about 20%, patients don't always feel a benefit possibly due to the indiscriminate selection of tissue being resected, there is a high degree of surgical trauma, and it is difficult to predict which patients will feel a benefit. Therefore LVRS is not a practical solution and inarguably some other approach is needed. The attention on LVRS has created some new ideas on non-surgical approaches to lung volume reduction. These approaches are presently in experimental phases and are reviewed below.

New minimally invasive lung volume reduction methods described in the prior art includes U.S. Pat. Nos. 5,972,026; 6,083,255; 6,174,323; 6,488,673; 6,514,290; 6,287,290; 6,527,761; 6,258,100; 6,293,951; 6,328,689; 6,402,754; 0020042564; 0020042565; 0020111620; 0010051799; 0020165618; and foreign patents EP1078601; WO98/44854; WO99/01076; WO99/32040; WO99/34741; WO99/64109; WO0051510; WO00/62699; WO01/03642; WO01/10314; WO01/13839; WO01/13908 WO01/66190.

Patent # 6328689 describes a method wherein lung tissue is sucked and compressed into a compliant sleeve placed into the pleural cavity through an opening in the chest. While this method may be less traumatic than LVRS it presents new problems. First, it will be difficult to isolate a bronchopulmonary segment for suction into the sleeve. In a diseased lung the normally occurring fissures that separate lung segments are barely present. Therefore, in order to suck tissue into the sleeve as proposed in the referenced invention, the shear forces on the tissue will cause tearing, air leaks and hemorrhage. Secondly the compliant sleeve will not be able to conform well enough to the contours of the chest wall therefore abrading the pleural lining as the lung moves during the breathing, thus leading to other complications such as adhesions and pleural infections.

U.S. Patent applications 2002/0147462 and 2001/0051799 explain methods wherein adherent substances are introduced to seal the bronchial lumen leading to a diseased area. It is proposed in these inventions that the trapped gas will dissipate with time. The main flaw with this method is that trapped gas will not effectively dissipate, even given weeks or months. Rather, a substantial amount of trapped gas will remain in the blocked area and the area will be at heightened infection risk due to mucus build up and migration of aerobic bacteria. Gas will not dissipate because: (1) blood perfusion is severely compromised, exacerbated by the Euler reflex, hence reducing gas exchange; (2) the tissue has low diffusivity for $CO_2$; and (3) additional gas will enter the blocked area through intersegmental collateral flow channels from neighboring areas. Another disadvantage with this invention is adhesive delivery difficulty; Controlling adhesive flow along with gravitational effects make delivery awkward and inaccurate. Further, if the adhesive is too hard it will be a tissue irritant and if the adhesive is too soft it will likely lack durability and adhesion strength. Some inventors are trying to overcome these challenges by incorporating biological response modifiers to promote tissue in-growth into the plug, however due to biological variability these systems will be unpredictable and will not reliably achieve the relatively high adhesion strength required. A further disadvantage with an adhesive bronchial plug, assuming adequate adhesion, is removal difficulty, which is extremely important in the event of post obstructive pneumonia unresponsive to antibiotic therapy, which is likely to occur as previously described.

U.S. Pat. No. 5,972,026 describes a method wherein the tissue in a diseased lung area is shrunk by heating the collagen in the tissue. The heated collagen fibers shrink in response to the heat and then reconstitute in their shrunk state. However, a flaw with this method is that the collagen will have a tendency to gradually return towards its initial state rendering the technique ineffective.

U.S. Pat. Nos. 6,174,323 and 6,514,290 describe methods wherein the lung tissue is endobronchially retracted by placing anchors connected by a cord at distal and proximal locations then shortening the distance between the anchors, thus compressing the tissue and reducing the volume of the targeted area. While technically sound, there are three fundamental physiological problems with this method. First, the rapid mechanical retraction and collapse of the lung tissue will cause excessive shear forces, especially in cases with pleural adhesions, likely leading to tearing, leaks and possibly hemorrhage. Secondly, distal air sacs remain engorged with $CO_2$ hence occupy valuable space without contributing to gas exchange. Third, the method does not remove trapped air in bullae. Also, the anchors described in the invention are not easily removable and they will likely tear the diseased and fragile tissue.

U.S. Patent Applications 2002/0042564, 2002/0042565 and 2002/0111620 describe methods where artificial channels are drilled in the lung parenchyma so that trapped air can then communicate more easily with the conducting airways and ultimately the upper airways, and/or to make intersegmental collateral channels less resistive to flow, so that $CO_2$-rich air can be expelled better during respiration. Its inventors propose that this method may be effective in treating homogeneously diffuse emphysema by preventing air trapping throughout the lung, however the method does not appear to be feasible because of the vast number of artificial channels that would need to be created to achieve effective communication with the vast number lobules trapping gas.

U.S. Pat. Nos. 6,293,951 and foreign patent WO01/66190 describe placing a one-way valve in the feeding bronchus of the diseased lung area. The proposed valves are intended to allow flow in the exhaled direction but not in the inhaled direction, with the intent that over many breath cycles, the trapped gas in the targeted area will escape through the valve thus deflating the lung compartment. This mechanism can be only partially effective due to fundamental lung mechanics, anatomy and physiology. First, because of the low tissue elasticity of the targeted diseased area, a pressure equilibrium is reached soon after the bronchus is valved, leaving a relatively high volume of gas in the area. Hence during exhalation there is an inadequate pressure gradient to force gas proximally through the valve. Secondly, small distal airways still collapse during exhalation, thus still trapping air. Also, the area will be replenished with gas from neighboring areas through intersegmental channels, trapped residual $CO_2$-rich gas will not completely absorb or dissipate over time and post-obstructive pneumonia problems will occur as previously described. Finally, a significant complication with a bronchial one-way valve is inevitable mucus build up on the proximal surface of the valve rendering the valve mechanism faulty.

U.S. Pat. Nos. 6,287,290 and 6,527,761 describe methods for deflating a diseased lung area by first isolating the area from the rest of the lung, then aspirating trapped air by applying vacuum to the bronchi in the area, and plugging the bronchus either before or after deflation. These methods also describe the adjunctive installation of Low Molecular Weight gas into the targeted area to facilitate aspiration and absorption of un-aspirated volume. It is appreciated in these inventions that the trapped air in the lung is not easily removable, and that aspiration of the trapped air may require sophisticated vacuum control. While apparently technically, physiologically and clinically sound, these methods still have some inherent and significant disadvantages. First, aspiration of trapped air by negative pressure is extremely difficult and sometimes impossible because mucus in the distal airways will instantly plug the airways when vacuum is applied because of the vacuum-induced constriction of the fragile airways. Also, it is difficult to avoid collapse of the distal airways when they are exposed to vacuum due to their diseased in-elastic state. Special vacuum parameters may enhance aspiration effectiveness by attempting to mitigate airway collapse, but the parameters will likely be different for different lung areas, for different times and for different patients because effective vacuum parameters will depend on the condition of hundreds of minute airways communicating with the trapped gas. These airways, although theoretically in parallel with one another, empirically do not behave in unison as one collective airway, but rather as many individual dynamic systems. Therefore, aspiration of an effective volume of trapped air using vacuum may be impractical to implement. Secondly, a vacuum technique will not remove the excessively trapped air in bullae. Third, the collapse-by-aspiration techniques described in these patents explain a relatively rapid deflation of the targeted area conducted while a clinician is attending to the instruments introduced into the lung, for example generally less than thirty minutes, which is the time a patient can tolerate the bronchoscopic procedure. Collapse-by-aspiration in this short a time period will often produce traumatic tissue shearing between the collapsing and non-collapsing areas, leading to tearing, leaks and hemorrhage, especially if there are adhesions and bullae present. Forth, although installation of low molecular weight gas may facilitate collapse by absorption, infusion of respiratory gases from neighboring lung areas through intersegmental collateral channels will refill the targeted lung area rending collapse incomplete. Some additional disadvantages of this technique include post-obstructive pneumonia, assuming incomplete air removal; the technique requires constant attendance of clinician which is impractical if a slow, gradual collapse of the lung area is desired; and finally the technique will be limited to large lung sections because suctioning requires a relatively large catheter inner diameter in order to avoid mucus plugging of the instruments.

To summarize, methods for minimally invasive lung volume reduction are either ineffective in collapsing the hyperinflated lung areas, or do not remove air in bullae, or collapse tissue too rapidly causing shear-related injury, or cause post-obstructive pneumonia.

The present invention disclosed herein takes into consideration the problems and challenges not solved by the aforementioned prior art methods in treating COPD and emphysema. In summary, this invention accomplishes (1) effective collapse of the targeted bronchopulmonary compartment including bullae by keeping the airways of the targeted area open by applying positive pressure to them and employing gas diffusion laws, (2) a gradual controlled atraumatic collapse of the targeted bronchopulmonary compartment thus avoiding the shearing issues associated with attempted rapid collapse, (3) avoidance of re-inflation by gas inflow through collateral channels using pressure gradients and gas diffusion laws, and (4) avoidance of post obstructive pneumonia. These methods and devices thereof are described below in more detail.

BRIEF SUMMARY OF THE INVENTION

The present invention provides a method for treating COPD or emphysema by reducing the volume of a targeted lung area (TLA), or bronchopulmonary compartment, using a desufflation[1] technique. In general bronchopulmonary compartment desufflation ("BCD" or "desufflation") is performed by (a) catheterizing the TLA, then (b) displacing the trapped $CO_2$-rich gas in the TLA by insufflating with a readily diffusible low molecular weight (DLMW) gas, then (c) pressurizing the DLMW gas in the TLA to a pressure greater than neighboring lung areas by delivering more DLMW gas into the targeted TLA and regulating pressure and gas concentration gradients favorable to diffusion out of the TLA while preventing infusion of respiratory gases, thereby causing a volumetric reduction of the TLA. In further embodiments the deflated TLA is restrained from re-expansion by tethering the tissue, or clamping the tissue, or blocking airflow into the tissue with an endobronchial plug.

[1] Desufflation: (n; v-desufflate) A volumetric reduction of a space caused by first displacing native fluid in the space by insufflating with a readily diffusible fluid which then effuses out of the space effecting reduction.

More specifically in a preferred embodiment of the present invention the feeding bronchus of the targeted TLA is catheterized with an indwelling catheter anchored in the bronchus such that it can remain in place for extended periods without being attended by a person. The catheter enters the bronchial tree from the upper airway, either through an artificial airway, such as a tracheal tube, or through a natural airway, such as the nasal passage, or through a percutaneous incision, such as a cricothyrotomy, and is advanced to the targeted TLA through the bronchial tree with endoscopic or fluoroscopic guidance. For ventilation and hygiene considerations, the catheter entry point into the body typically includes a self-sealing and tensioning connector that prevents fluid from escaping from around the catheter shaft, but which permits axial catheter sliding to compensate for patient movement or for elective catheter repositioning. The tensioning connector also prevents inadvertent dislodging of the catheter's distal end anchor from the bronchus. In accordance with this embodiment the catheter includes at least one lumen through which a DLMW gas is delivered into the targeted TLA to displace the native gas while also providing a pathway for exhausting of mixed gases exiting the TLA. The DLMW gas delivery is regulated to create a sustained average positive pressure in the TLA and hence a pressure gradient favorable to gas exhausting. The gas displacement procedure is continued for a sufficient duration, between one hour and 14 days, to gradually displace a substantial percentage of native gases, including trapped gas in Bulla, thus resulting in a predominate DLMW gas composition.

In a further embodiment of the present invention, a vacuum is applied to a lumen in the catheter to facilitate exhaust of mixed gases and displacement of native gas however without creating negative pressure in the TLA, which would collapse the airways, and without disrupting the sustained periods of positive pressure in the TLA which are absolutely critical to prevent airway collapse so that proper gas mixing and displacement can occur. Optionally a vacuum can be applied to bronchi of neighboring lung areas to assist gas wash out and effusion from the targeted TLA into neighboring lung areas through intersegmental collateral channels.

Still in accordance with the preferred embodiment of the present invention, after a predominant concentration of DLMW gas is reached in the TLA the, DLMW gas pressure in the TLA is regulated to an elevated but safe level above the pressure in neighboring lung areas so as to create a pressure gradient favorable to gas transfer out of the TLA into neighboring areas through tissue, collateral channels and, if available, vasculature. This is accomplished by instilling additional DLMW gas. Typical TLA pressures are initially set at 10-25 $cmH_2O$ or 25-50 $cmH_2O$ in spontaneously breathing patients or mechanically ventilated patients respectively thus creating an initial mean pressure gradient between the targeted TLA and neighboring compartments of approximately 20 $cmH_2O$. The elevated TLA pressure also prevents influx of respiratory gases through collateral channels or other sources. Gradually, the amplitude of the pressure gradient is lowered by regulation of the TLA pressure and controlling the amount of new DLMW gas delivery via the catheter. First, because of the net efflux of gas out of the lobules through interconnecting channels in the alveoli (pores of Kohn) and terminal bronchioles (Lambert's canals) and then out of the TLA through intersegmental channels the lobules begin to reduce in size causing an overall shrinkage and consolidation of tissue, thus decreasing the diffusivity of the tissue to influx of larger molecule respiratory gases (such as $CO_2$ and $N_2$). Eventually, alveoli and entire lobules collapse thus substantially deflating the TLA and after further consolidation, the tissue and intersegmental collateral channels become non-diffusible to incoming respiratory gases. Further, due to the surface tension of the collapsed air pockets they resist re-opening and long term and/or permanent collapse is possible. The duration of this diffusion/deflation procedure is controlled to obtain a slow rate of deflation such that the resultant tissue shear forces are benign and atraumatic and such that even the DLMW gas in the bullae has sufficient duration to effuse. This is expected to take between 1 hour and 30 days, most typically 7 to 14 days depending on the size of the TLA compartment, the size and number of bulla, the level and variability of the disease, and the selected desufflation parameters. The duration is designed and controlled such that the rate of deflation is about the same rate of tissue remodeling, such that the two can occur concurrently thus mitigating shear induced injury.

In an additional embodiment of the present invention, regulation of the TLA pressure, during the native gas displacement phase and/or during the DLMW gas diffusion/deflation phase, is further facilitated by occluding the annular space between the catheter and the feeding bronchus of the TLA. This embodiment further facilitates control of the pressure and gas concentration in the TLA particularly in gravitationally challenging situations. In a yet additional embodiment of the present invention, the pressure profiles of DLMW gas delivery and respiratory gas exhaust are regulated to be either constant, variable, intermittent, oscillatory, or synchronized with the patient's breathing pattern. It can be appreciated that the possible combinations of pressure profiles are extensive, but all must comply with the following fundamental and critical principle that is unique to the present invention: The pressure profiles must create and maintain a pressure gradient of higher pressure in the TLA than that in neighboring areas for extended periods to facilitate more gas efflux then influx and must keep the hundreds of small distal airways open thus creating sustained communication with the otherwise trapped gas in the distal spaces during the various phases of the desufflation procedure.

Still in accordance with the preferred embodiment of the present invention, the proximal end of the catheter is kept external to the patient and is connected to a desufflation gas control unit (DGCU). The DGCU comprises a supply of DLMW gas, or alternately an input connection means to a supply thereof, and comprises the requisite valves, pumps, regulators, conduits and sensors to control the desired delivery of the DLMW gas and to control the desired pressure in the TLA. The DGCU may comprise a replaceable or refillable modular cartridge of compressed pressurized DLMW gas and/or may comprise a pump system that receives DLMW gas from a reservoir and ejects the DLMW gas into the TLA through the catheter at the desired parameters. The DGCU further comprises fail-safe overpressure relief mechanisms to avoid risk of lung barotrauma. The DGCU may also comprise a negative pressure generating source and control system also connectable to a lumen in the catheter for the previously described facilitation of native gas exhaust. The DGCU may be configured to be remove-ably or permanently attached to a ventilator, internally or externally, or to be worn by an ambulatory patient. It is appreciated that the DGCU will have the requisite control and monitoring interface to allow the user to control and monitor the relevant parameters of the desufflation procedure, as well as the requisite power source, enclosure, etc.

It should be noted that in some embodiments of this invention, desufflation is performed during mechanical ventilation to more effectively ventilate a patient, for example to assist in weaning a patient from ventilatory support. Still in other cases, desufflation is performed as a chronic therapy either continuously or intermittently on a naturally breathing patient. In this later embodiment, the catheter may be removed after a treatment while leaving a hygienic seal at the percutaneous access point, and a new catheter later inserted for a subsequent treatment. Still in other embodiments of this invention, it is necessary to restrain the TLA from re-expansion in order to achieve the desired clinical result, such as but not limited to a bronchial plug, a tissue tether or a tissue clamp. It should also be noted that the desufflation procedure may be performed simultaneously on different lung areas or sequentially on the same or different lung areas. Finally it should be noted that the desufflation procedure can be performed on a relatively few large sections of lung, for example on one to six lobar segments on patients with heterogeneous or bullous emphysema, or can be performed on many relatively small sections of lung, for example on four to twelve sub-subsegments on patients with diffuse homogeneous emphysema.

The basic scientific principles employed to accomplish desufflation are the physical laws of mass transfer, ie., gas and tissue diffusivity, concentration gradients and pressure gradients, and the physical laws of collapsible tubes. As can be seen in a review of the prior art, no methods currently exist wherein a lung area hyperinflated with trapped $CO_2$-rich gas is deflated by creating and maintaining an elevated positive pressure in the said area with diffusible gas nor wherein the said area is deflated by pressurizing the airways in the area to push gas out of the treated area through collateral pathways.

BRIEF DESCRIPTION OF THE DRAWINGS

FIG. 2 describes the physics governing desufflation.

FIG. 3a graphically shows the diffusible gas delivery flow rate being delivered into the treatment area during the gas wash out stage and the volume reduction stage.

FIG. 3b graphically shows the diffusible gas delivery pressure being delivered into the treatment area during the gas wash out stage and the volume reduction stage FIG. 3c graphically shows the gas pressure in the treatment area during the gas wash out stage and the volume reduction stage.

FIG. 3d graphically shows the increasing and decreasing diffusible and respiratory gas concentrations in the treatment area, during the gas wash out stage and the volume reduction stage.

FIG. 3e graphically shows the residual volume reduction of the treatment area during the gas wash out and volume reduction stages.

FIG. 5a depicts the various gas flow pathways for influx and efflux of gases

FIG. 5b depicts a catheter with a non-occlusive anchor.

FIG. 5c depicts a catheter with an intermittently inflatable occlusive anchor and with gas delivery and gas removal lumens.

FIG. 5d depicts a catheter with an intermittently inflatable occlusive anchor and with a shared lumen for gas delivery and removal.

FIG. 5e depicts a catheter with concentric lumens with a gas delivery inner lumen and a gas removal outer lumen.

FIG. 7a describes a non-occlusive wire basket catheter anchor.

FIG. 7b describes an inflatable non-occlusive catheter anchor.

FIG. 7c describes an intermittently inflatable and occlusive anchor.

FIG. 7d describes a combination non-occlusive wire basket catheter anchor and an intermittently inflatable occlusive anchor.

FIG. 7e describes an catheter with an inner member with a non-occlusive anchor.

FIG. 8 is a general layout of desufflation being performed on a ventilatory dependent patient.

FIG. 9 is a general layout of desufflation being performed on an ambulatory spontaneously breathing patient.

FIG. 9a is a cross sectional view showing a sealing and securing sleeve at the catheter access site into the patient.

FIG. 11 describes a desufflation procedure kit.

DETAILED DESCRIPTION OF THE INVENTION

Figure 1:
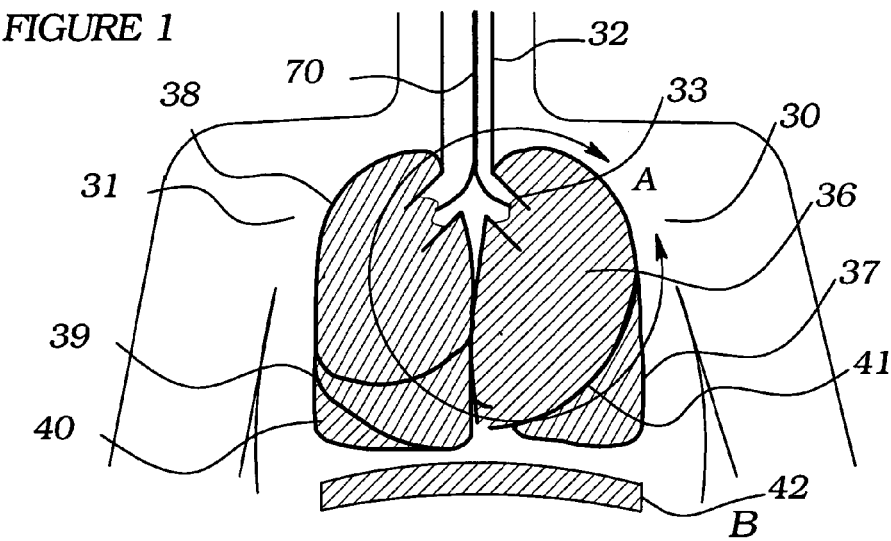
FIG. 1 describes a partial cross sectional view of a patient's chest and lungs describing the lung anatomy.
Figure 1A:
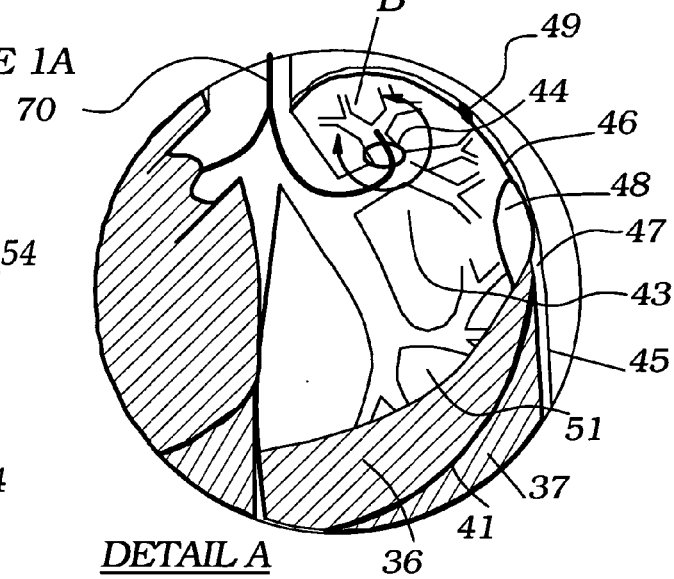
FIG. 1a describes a cross sectional view of the lung showing placement of the desuflation catheter in a lung bronchi.
Figure 1B:
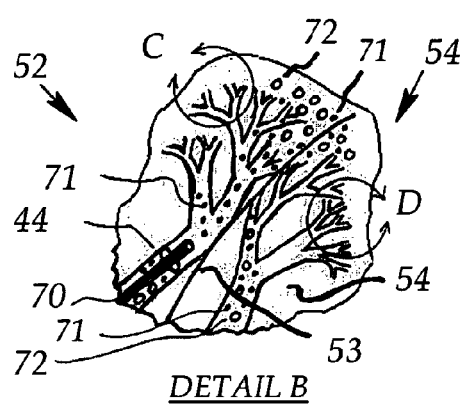
FIG. 1b describes the delivery, exhausting, and diffusion of the diffusible low molecular weight gas in the treated lung area.
Figure 1C:
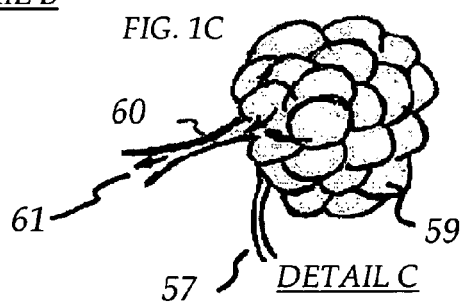
FIG. 1c describes an emphysematous lung area with enlarged poorly defined alveoli.
Figure 1D:
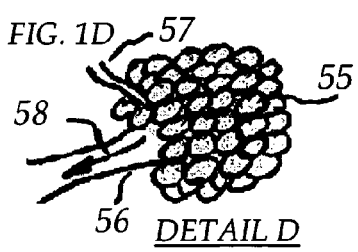
FIG. 1d describes a healthy lung area with properly sized and well defined alveoli.
Figure 4A:
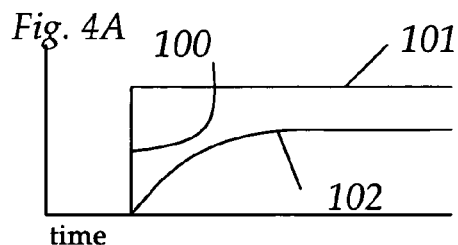
FIG. 4a graphically describes the diffusible gas flow and pressure delivery at constant amplitude.
Figure 4B:
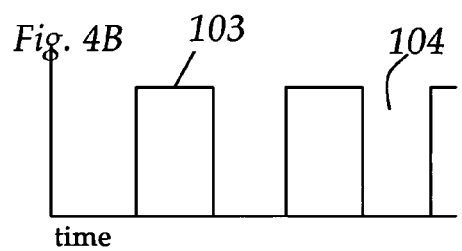
FIG. 4b graphically describes the delivery of diffusible gas with an intermittent delivery cycle.
Figure 4C:
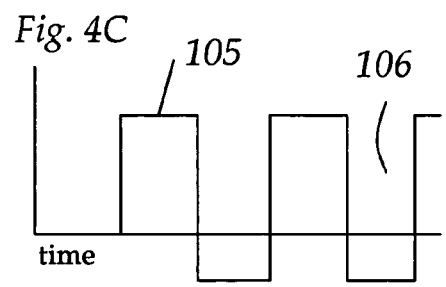
FIG. 4c graphically describes the delivery of diffusible gas with a positive pressure alternating with the removal of mixed gas using a negative pressure.
Figure 4D:
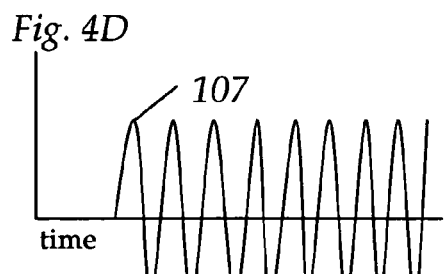
FIG. 4d graphically describes oscillatory delivery of diffusible gas, alternating with negative pressure removal of mixed gases.
Figure 4E:
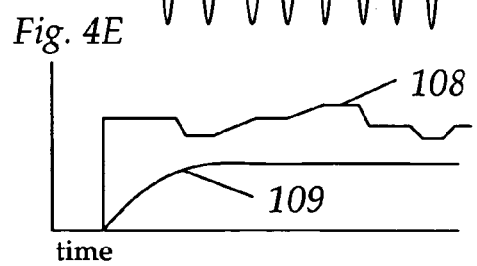
FIG. 4e graphically describes a continuously adjusting delivery level of diffusible gas.
Figure 4F:
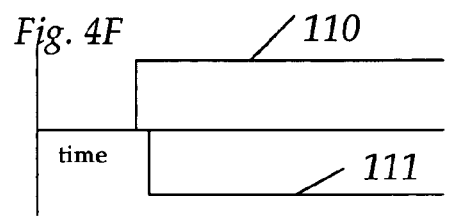
FIG. 4f graphically describes simultaneous positive pressure delivery of diffusible gas with vacuum removal of mixed gases.
Figure 4G:
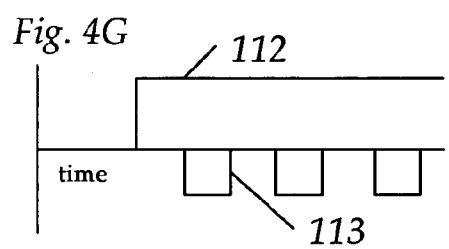
FIG. 4g graphically describes simultaneous constant amplitude delivery of diffusible gas with oscillatory vacuum removal of mixed gases.
Figure 4H:
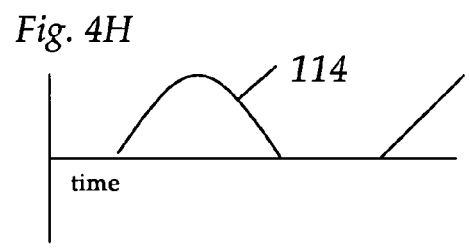
FIG. 4h graphically describes increasing and decreasing slopes of diffusible gas delivery.
Figure 4I:
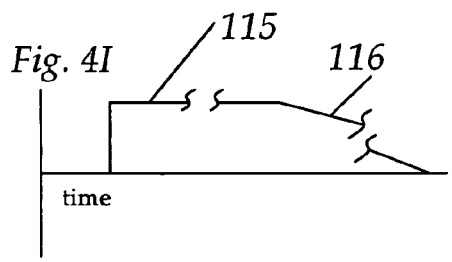
FIG. 4i graphically describes a constant amplitude delivery of diffusible gas during the gas wash out stage and a decreasing amplitude delivery during the volume reduction stage.
Figure 4J:
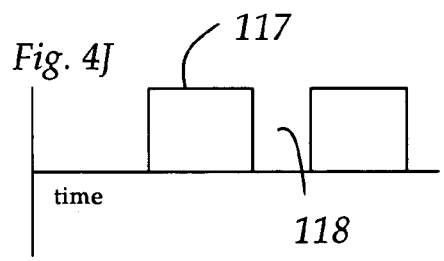
FIG. 4j graphically describes diffusible gas delivery synchronized with the breathing cycle.

Referring to FIGS. 1-1d the desufflation procedure is summarily described being performed in an emphysematous lung. FIG. 1 shows the left 30 and right 31 lung, trachea 32, the left main stem bronchus 33, the five lung lobes 36, 37, 38, 39, 40, a lateral fissure 41 separating the left upper and lower lobe, and the diaphragm 42 which is displaced downward due to the hyperinflated emphysematous lung. Detail A in FIG. 1a shows a cut away view in which the upper left lobe bronchus 43, the apical segmental bronchus 44 of the left upper lobe, the parietal pleura 45, the visceral pleura 46, the pleural cavity 47, a large bulla 48 and adhesions 49. Bullae are membranous air vesicles created on the surface of the lung between the visceral pleura 46 and lung parenchyma 51 due to leakage of air out of the damaged distal airways and through the lung parenchyma. The air in the bullae is highly stagnant and does not easily communicate with the conducting airways making it very difficult to collapse bullae. Pleural tissue adhesions 49 are fibrous tissue between the visceral pleura 46 and the parietal pleura 45 which arise from trauma or tissue fragility. These adhesions render it difficult to acutely deflate an emphysematous hyperinflated lung compartment without causing tissue injury such as tearing, hemorrhage or pneumothorax. Detail B in FIG. 1b describes the bronchi 44 of the left upper lobe apical segment 52 and a separation 53 between the apical segment and the anterior segment 54. Detail D in FIG. 1d a non-emphysematous lung lobule is shown which includes the functional units of gas exchange, the alveoli 55, and $CO_2$-rich exhaled gas 58 easily exiting the respiratory bronchiole 56, Also shown are intersegmental collateral channels 57, typically 40-200 um in diameter, which communicate between bronchopulmonary segments making it difficult for a lung compartment to collapse or remain collapsed because of re-supply of air from neighboring compartments through these collateral channels. Detail C in FIG. 1c describes an emphysematous lung lobule in which the alveolar walls are destroyed from elastin breakdown resulting in large air sacks 59. The emphysematous lobule traps air becoming further hyperinflated because the respiratory bronchiole leading to the engorged lobule collapses 60 during exhalation, thus allowing air in but limiting air flow out 61.

FIGS. 1, 1a, 1b also shows the desufflation catheter 70 anchored in the apical segment bronchus 44. In FIG. 1b, DLMW gas 71 is shown being delivered by the desufflation catheter 70. The native gas 72 in the targeted apical segment is forced out of the apical segment 52, both proximally alongside the catheter 70 and also across intersegmental collateral channels into the neighboring anterior segment 54 then proximally up the airways. The DLMW gas 71 also is forced through the intersegmental collateral channels in the same manner. The application and maintenance of a pressure gradient of a higher but safe pressure in the treated area compared to the neighboring area assures that the bronchioles in the treated area do not collapse during the procedure so that air is not trapped in the distal areas.

Now referring to FIG. 2, a mass transfer schematic 78 and mathematical model 79 is shown describing the governing physics and the fundamental importance of the pressure and concentration gradient that is critical to the desufflation procedure. DLMW gas is delivered to the targeted lung area 80 and native gas and DLMW gas effuses into the neighboring lung areas 81.

FIG. 3 describes the DLMW gas flow delivery, gas concentration and gas volume profiles for a typical desufflation procedure. FIGS. 3a and 3b describe the delivered DLMW gas flow and pressure respectively during the gas wash out phase 85 and 87, which may be a constant amplitude and during the deflation phase 86 and 88, when the gas flow and pressure is reduced over time.

FIG. 3c describes the resultant gas pressure that is created by desufflation in the targeted lung area 89 which is typically maintained at level higher than the gas pressure in neighboring lung areas 90. During the deflation phase the targeted lung area pressure is reduced 91 as deflation occurs.

FIG. 3d describes the gas concentration in the targeted lung area wherein the native gas concentration 92 attenuates while the DLMW gas concentration 93 increases. During the deflation stage, the DLMW gas concentration 95 is close to 100% and the native gas concentration 94 is close to 0%.

FIG. 3e describes the targeted area gas volumes which are initially very high due to the disease, and are kept high during the gas wash out phase 96 with the installation of DLMW gas. During the deflation stage, after most of the native gas is washed out, the targeted area gas volume is regulated downward 97 as the positive pressure of DLMW gas delivery is regulated downward.

Now referring to FIG. 4, different optional desufflation gas pressures and flow profiles are described. In FIG. 4a after the start of the desufflation procedure 100 the gas flow 101 and resultant gas pressure 102 are shown at constant amplitude. In FIG. 4b an intermittent delivered flow is shown indicating an on 103 and off 104 period. FIG. 4c describes an alternating positive pressure 105 and negative pressure 106 delivery. FIG. 4d describes an oscillating 107 pressure or flow delivery. FIG. 4e describes a DLMW gas flow delivery that is continuously adjusted 108 in order to maintain a constant level positive pressure 109 in the targeted lung area. FIG. 4f describes simultaneous positive pressure delivery of DLMW gas 110 and application of vacuum 111 to exhaust mixed gases from the targeted lung area. FIG. 4g describes constant level DLMW gas delivery 112 simultaneous with intermittent or oscillatory vacuum application for exhaust 113. FIG. 4h describes an ascending and descending waveform 114 of DLMW gas pressure or flow delivery. FIG. 4I describes the gas wash out stage of DLMW gas delivery 115 where the delivered pressure may be constant and the deflation stage of DLMW gas delivery 116 where the delivered pressure may be reduced. FIG. 4j describes DLMW gas delivery that is synchronized with the patient's breathing; In this case DLMW gas is delivered during exhalation 117 and delivery is interrupted during inspiration 118.

Desufflation pressure is typically regulated below 50 cmH$_2$O to avoid barotrauma and to avoid inadvertent creation of bulla and to avoid creating inadvertent embolism in the vasculature, and typically above 10 cmH$_2$O in order to maintain the requisite pressure gradient. The duration for native gas displacement typically ranges from 1 hour to 14 days depending on the lung area size and number of bulla. The duration for DLMW gas effusion/deflation is typically regulated to take from 1 day to 30 days, depending on the lung area size and number of bulla, such that neighboring lung tissue has sufficient duration to remodel simultaneously with targeted area deflation, to avoid tissue injury caused by rapid collapse.

Now referring to FIG. 5, gas flow pathways and alternative catheter configurations for the desufflation procedure are described in more detail. FIG. 5a graphically describes the gas flow pathways for influx and efflux of gases. DLMW gas is delivered 130 into the targeted lung area via the catheter. Also, some respiratory gases from breathing 131 continue to enter the targeted lung area during the procedure although at a reducing rate over time since the area will become filled with DLMW gas 130. Some of the delivered DLMW gas escapes from the targeted area around the catheter 132 proximally out the airways proximal to the targeted area. The majority of native gases in the targeted area are forced out proximally around the catheter 133 and this efflux of native gases dramatically reduces over time because the content of native gas in the targeted area are significantly reduced. Meanwhile, gases are forced out of the targeted area through collateral channels into neighboring lung areas since the desufflation parameters have created a pressure gradient in that direction. Native gas effusion through collateral channels 135 reduces towards zero in the gas wash out stage of the procedure, while DLMW gas effusion through collateral channels 134 remains constant during the gas wash out stage and is deliberately reduced during the deflation stage as the desufflation parameters are appropriately regulated.

FIGS. 5b, 5c, 5d and 5e depict alternate catheter configurations corresponding to alternative means of controlling the desufflation parameters. FIG. 5b depicts a catheter with a non-occlusive anchor 150 and single lumen 151 for DLMW gas infusion, mixed gas evacuation occurring around the catheter 152. FIG. 5c depicts a catheter with an occlusive anchor 153 and with separate lumens for DLMW gas infusion 154 and mixed gas evacuation 155. FIG. 5d depicts a catheter with an occlusive anchor 156 wherein DLMW gas infusion and mixed gas evacuation is conducted through a common lumen 157 by alternating between infusion and exhaust. FIG. 5e describes a catheter with a infusion lumen 158 and ports 159 for application of vacuum 160 to be applied to neighboring bronchi 162 to facilitate efflux of gas 161 out of the targeted lung area via collateral channels. It can be appreciated that many configurations of lumens, occlusive anchors and pneumatic parameters can be combined in many ways to achieve different optional desufflation techniques.

Figure 6:
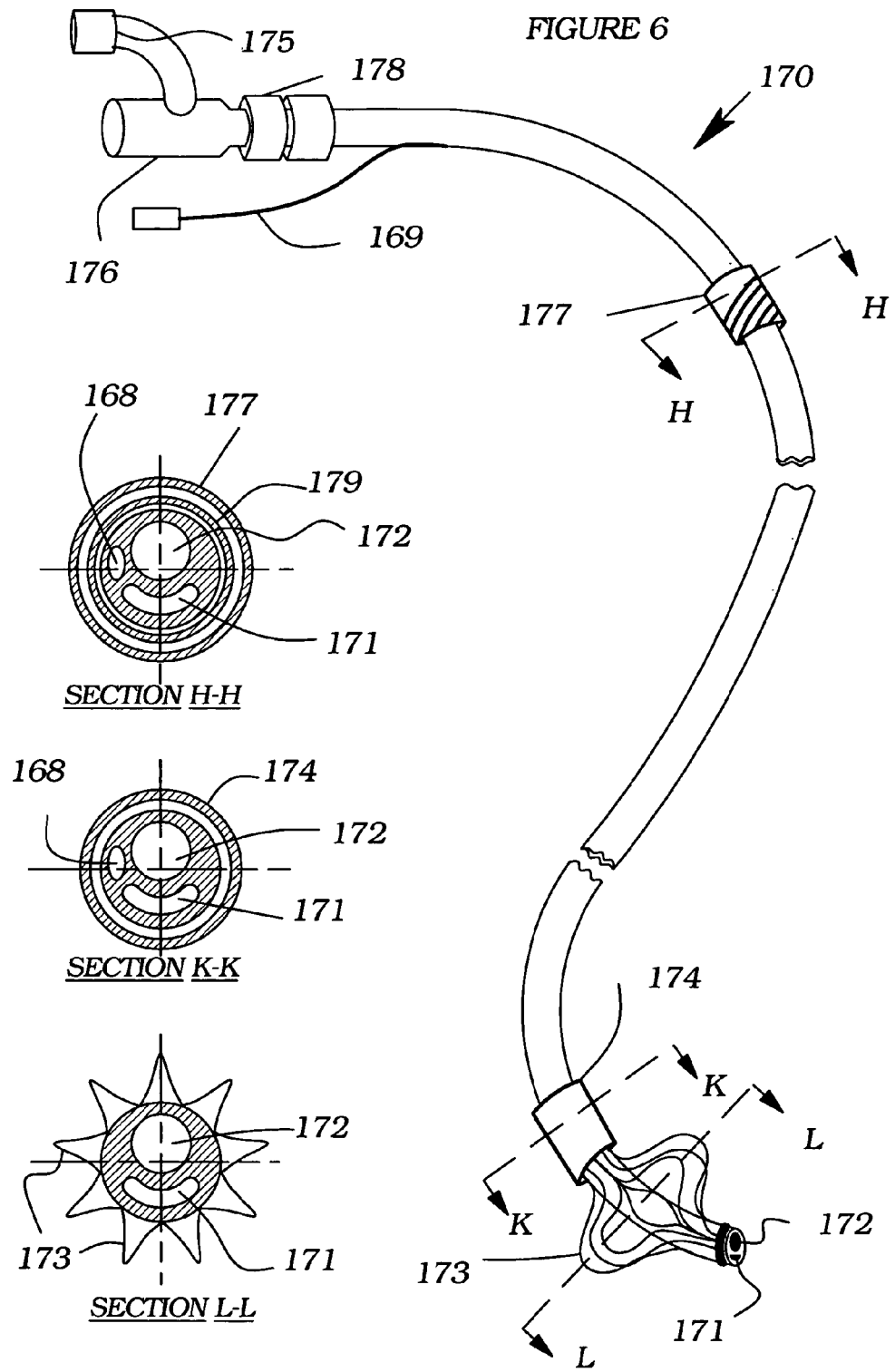
FIG. 6 describes a typical desufflation catheter.

Now referring to FIG. 6, a typical desufflation catheter 170 is described including a DLMW gas flow lumen 171, optionally an exhaust gas lumen 172, a non-occlusive anchoring means 173 and a sleeve 174 for collapsing the anchoring means, a slide mechanism 169 and lumen for the mechanism 168 for retracting the sleeve 174, a connector at its proximal end for attachment to a and a supply of DLMW gas 175 and optionally a vacuum source 176, a tensioning or sealing means 177 with a sealing ring 179 for tensioning and optionally sealing at the point of entry into the patient, and a connection means 178 near the proximal end for detachment of the proximal end from the shaft, for example if removing an endoscope from over the catheter or for interrupting the therapy while leaving the distal end of the catheter in-situ.

Figure 7:
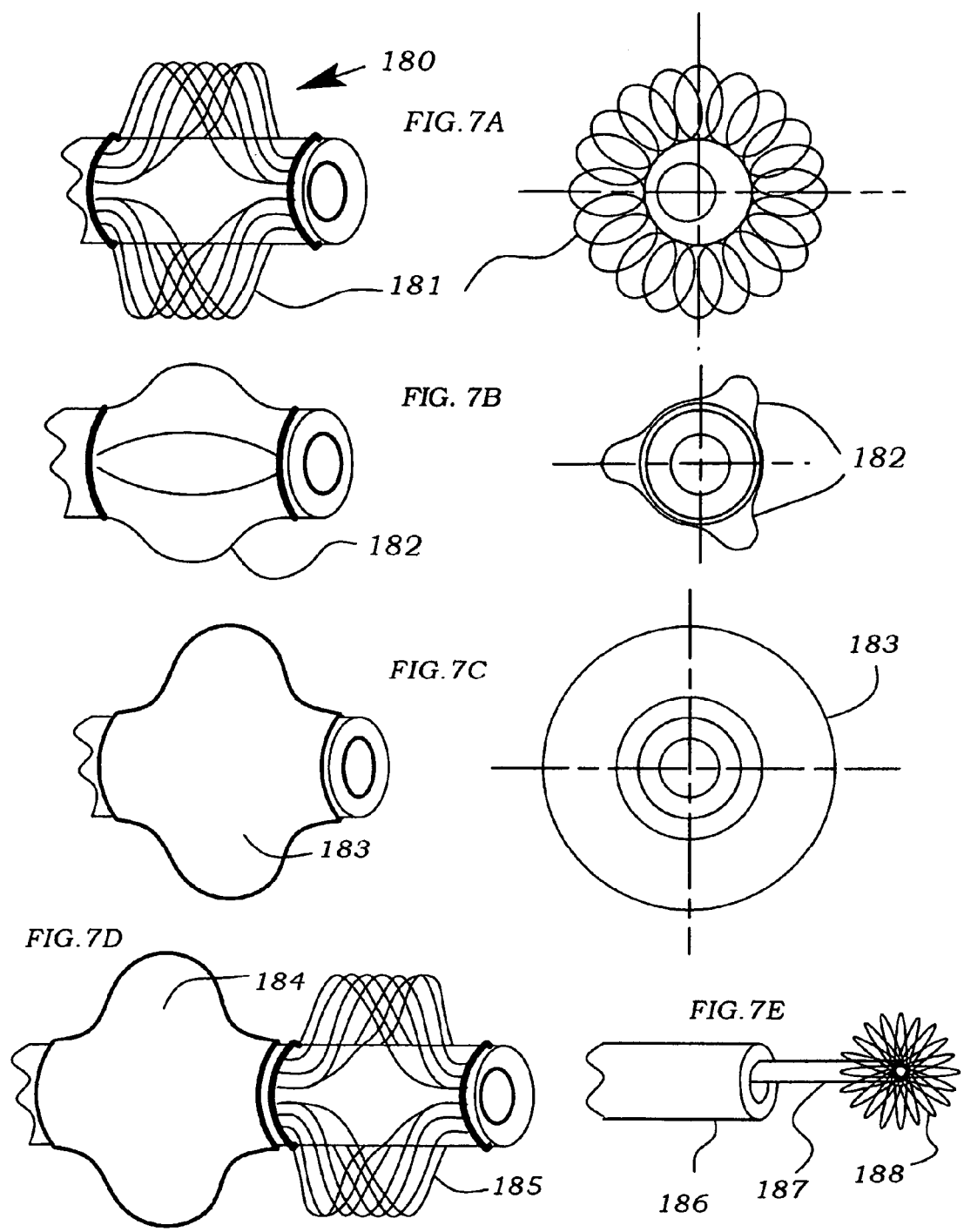
FIG. 7 describes different catheter anchoring configurations.

FIG. 7 depicts alternative anchor configurations. FIG. 7a describes a radially expanding and compressible wire coil anchor 180 in which the wires 181 are braided to create a cylindrical structure that does not occlude the airway. FIG. 7b describes a radially inflatable anchor with spokes 182 such that the anchor does not occlude the airway. FIG. 7c describes a radially expanding inflatable anchor such as a cuff or balloon 183 which occludes the airway while anchoring. FIG. 7d describes a catheter with an occlusive sealing member 184 which can be continuously or intermittently inflated to facilitate regulation of the desufflation parameters in the TLA, and a non-occlusive anchor 185 to continuously anchor the catheter in the airway for extended periods. FIG. 7e describes an outer 186 and inner 187 catheter configuration wherein the inner catheter 187 is axially slide-able with respect to the outer catheter 186 and wherein the inner catheter includes a radially expandable anchoring member 188, such as a wire basket, for securing the catheter in position for extended periods. The inner catheter in this embodiment may include a thermoplastic material or may alternately include a metallic construction such as a guidewire.

Typical diameters of the desufflation catheter depend on the lung area being targeted. Some exemplary dimensions follow: Lobar segment: OD=2.0-3.5 mm; Lobar subsegment: OD=1.5-2.5 mm; Lobar sub-subsegment: OD=0.5-1.0 mm. DLMW gas insufflation lumen diameters are typically 0.25-1.0 mm and gas exhaust lumens, if present, are typically comprise an area of 0.8-4.0 mm$^2$, preferably greater than 2.0 mm$^2$ to avoid mucus plugging. Catheter lengths are typically 120-150 cm. Anchoring forces are typically 1-10 psi and occlusion forces, if present, are typically 0.2-0.5 psi. Proximal entry point tensioning forces typically produce 0.5-1.5 lbs of axial tension. Anchors and occlusive member diameters depend on the targeted bronchial level and are up to 20 mm for lobar bronchi, 15 mm for segmental bronchi and 5mm for sub-subsegmental bronchi when fully expanded. Some examples of catheter materials are: the shaft extrusion comprised of a thermoplastic or thermoset material, such as nylon, PVC, polyethylene, PEBAX, silicone; the non-occlusive anchor comprised of a stainless steel or Nitinol wire; the inflatable occlusive member comprised of a highly compliant plastisol, silicone or urethane; connectors typically comprised of PVC, polysulfone, polypropylene or acrylic.

FIG. 8 describes a general layout of the present invention, wherein Endotracheal Transluminal Bronchopulmonary Compartment Desufflation (ETBCD) is performed on a ventilatory dependent patient, showing catheterization of the targeted TLA 250, entry of the catheter 170 through an endotracheal tube 252, connection of the proximal end of the catheter 253 to the desufflation pneumatic control unit (PCU) 254, as well as the ventilator 255 and breathing circuit 256. It can be seen that the catheter distal end is anchored 257 in the targeted lung area bronchus and the section of catheter at the patient entry point is tensioned to prevent inadvertent unwanted movement with a tensioning and/or sealing means 177.

FIG. 9 describes a general layout of the present invention, wherein Percutaneous Transluminal Bronchopulmonary Compartment Desufflation (PTDCD) is performed on an ambulatory spontaneously breathing patient, showing catheterization of the targeted TLA with the desufflation catheter 170, distal end anchoring 261, entry of the catheter either nasally 262 or through a percutaneous incision 263, connection of the proximal end of the catheter to the wearable portable PCU 254. Referring to FIG. 9a a cross-sectional view is shown of entry of the catheter into the patient showing a hygienic seal 177 and a seal securing means 266 attached to the neck of the patient. The hygienic seal also prevents inadvertent unwanted axial movement of the catheter but allows desired axial sliding of the catheter in response to anticipated patient movement. The seal can be left in place to temporarily seal the incision with a self-sealing membrane or attaching a plug 267 if the catheter is removed for extended periods.

Figure 10:
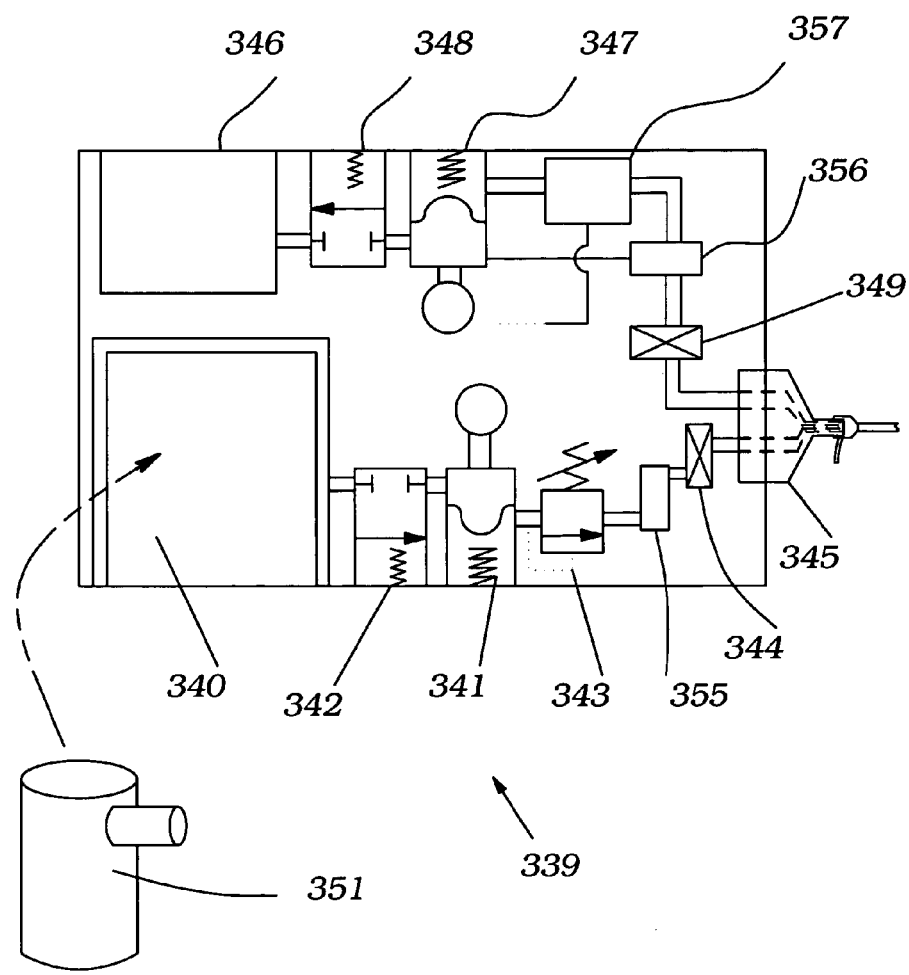
FIG. 10 describes the general layout of the desufflation pneumatic control unit (PCU).

Now referring to FIG. 10 the Desufflation Pneumatic Control Unit 339 (PCU) is shown in more detail, including a DLMW gas source 340, an insufflation pressure regulator 341, control valve 342, and overpressure safety relief valve 343, a check valve 344, a pressure sensor 355, and a self-sealing output DLMW gas connector 345. Also exemplified is a vacuum supply system comprised of a vacuum source 346, vacuum regulator 347, control valve 348, check valve 349, pressure sensor 356 and $CO_2$ sensor 357. A replaceable or refillable modular cartridge of DLMW gas 351 is shown as an alternative supply, typically housing 100-500 ml of compressed DLMW gas. For example a cartridge containing 250 ml of compressed DLMW gas pressurized at 10 psi would enable delivery of DLMW gas at a rate of 10 ml/hour at an output pressure of 25 cmH$_2$O for 20 days, based on ideal gas laws, and assuming 30% losses due to system leakage. A pump system 352 is shown as an alternative to a pressurized source in which case the DLMW gas is fed into the pump from the outside source and pumped out into the catheter at the desired output parameters.

FIG. 11 describes a desufflation procedure kit, including the desufflation catheter 170, optionally an inner catheter or guidewire 187, a tensioning connector 177, a securing strap 266, a hygienic tracheotomy plug 267, a bronchial plug 335 to prevent re-inflation of the desufflated lung area, a desufflation pneumatic control unit 339 with a holster 338, a cartridge of DLMW gas 351, pre-conditioning solutions 336, and an instruction sheet 337.

It should be noted that the above preferred embodiments of the present invention are exemplary and can be combined in mixed in ways to create other embodiments not specifically described but which are still part of this disclosure. For example, the catheter occlusive anchor can be detachable from the catheter so that after the desufflation procedure is complete, the catheter can be retracted from the airway, leaving the occlusive member in place which self seals in the airway thus preventing re-expansion of the treated area.

The invention claimed is:

1. A method for reducing the residual volume of a target lung area which is connected to neighboring lung areas with collateral airflow channels, the method further maintaining patency of and without obstructing the bronchii leading to the target lung area, said patency maintained in order to prevent post obstructive pneumonia the method comprising:
    a. placing the distal tip of an indwelling catheter in a feeding bronchus proximal to and ventilating said target lung area, wherein said catheter is anchored in said proximal feeding bronchus without occluding said bronchus, and wherein the catheter remains in place for an extended treatment period lasting longer than 30 minutes;
    b. causing a decrease in residual volume in the target lung area, the decrease causing a remodeling of neighboring lung areas, the decrease caused by displacing during the treatment period the native respiratory gases consisting of oxygen, CO2 and N2 naturally residing in the target lung area, displacing said gases by delivering through said catheter a diffusible low molecular weight (DLMW) gas which is at least twice as diffusible as the respiratory gases, wherein the diffusibility of the DLMW gas allows more volume of DLMW gas to diffuse through the collateral channels into neighboring lung areas compared to the volume of respiratory gas diffusing through the collateral channels into the target lung area from neighboring areas;
    c. maintaining an exhaust pathway external to the catheter, to allow the native respiratory gas and the DLMW gas to flow in the proximal exhalation direction out of the lung area through the proximal feeding bronchus over the treatment period.

2. A method as in claim 1 wherein said catheter anchoring permits said catheter to remain in place automatically for said extended treatment period without requiring being continuously observed by a clinician.

3. A Method as in claim 1 wherein said DLMW gas is delivered at a positive pressure, to create a gas pressure in the targeted lung area 2-20 cwp greater than the gas pressure in the neighboring lung areas.

4. A method as in claim 1 wherein said DLMW gas delivery is regulated to create a pressure in said targeted lung area that is at least temporarily 2-20 cwp greater than the gas pressure in neighboring lung areas to displace the native respiratory gas.

5. A method as in claim 1 wherein said DLMW gas delivery is regulated to create a pressure in said targeted lung area greater than the gas pressure in said neighboring lung areas, and further wherein said pressure in said targeted lung area is regulated to be reduced over a period until said targeted lung area pressure equals the pressure in said neighboring lung areas.

6. A method as in claim 1 wherein said catheter is placed through the user's natural upper airway while the user is spontaneously breathing.

7. A method as in claim 1 wherein said catheter is placed through an artificial airway tube.

8. A method as in claim 1 wherein multiple lung areas are treated simultaneously.

9. A method as in claim 1 wherein said proximal feeding bronchus is at the lung level between a subsegmental bronchus and a lobar bronchus, inclusive of the subsegmental and lobar bronchii.

10. A method as in claim 1 wherein said catheter is positioned using endoscopic visual assistance.

11. A method as in claim 1 wherein said proximal feeding bronchus of said target lung area remains un-occluded by said catheter and wherein the presence of said catheter in said proximal feeding bronchus reduces the amplitude of airflow in and out of said target lung area.

12. A method as in claim 1 wherein said catheter occludes said proximal feeding bronchus of said lung area intermittently to regulate the DLMW gas flow through the collateral channels.

13. A method as in claim 1 wherein said DLMW gas is delivered continuously at a constant pressure amplitude.

14. A method as in claim 1 wherein said DLMW gas is delivered with an intermittent flow pattern.

15. A method as in claim 1 wherein said gas flow in the proximal direction is actively assisted by the application of vacuum to said target lung area through a lumen in said catheter.

16. A method as in claim 1 wherein said residual volume reduction is augmented by the application of vacuum to neighboring lung areas, thereby augmenting gas flow through said collateral channels from said target lung area into said neighboring lung areas.

17. A method as in claim 1 wherein said gas flow in the proximal direction is conducted through a first lumen in said catheter, and DLMW gas delivery is conducted through a second lumen in said catheter.

18. A method as in claim 1 wherein said DLMW gas possesses diffusivity of at least $10^{-4}$ cm$^2$/sec and consists of a molecular weight of 2-20 atomic mass units to accomplish the desired rate and degree of residual volume reduction.

19. A method as in claim 1 wherein said DLMW gas delivery is performed as an extended acute procedure consisting of more than 2 hours.

20. A method as in claim 1 wherein a therapeutic agent is delivered to said target lung area after said native respiratory gas displacement.

21. A method for reducing the volume of a target lung area by delivering via a catheter, while maintaining predominantly patent airways leading to said target lung area, a positive pressure of Diffusible Low Molecular Weight (DLMW) gas into a said target lung area and creating a positive pressure of DLMW gas in said area, said positive pressure being predominantly greater than the pressure in neighboring lung areas, and wherein (a) said positive pressure of DLMW gas is created by delivering said DLMW gas via a catheter into said area, and (b) said gas delivery is regulated to achieve at least temporarily a desired pressure level of 2-20 cwp greater than the gas pressure in neighboring areas to achieve volume reduction at the desired rate and amount and (c) said delivery is performed over extended periods consisting of greater than two hours to achieve volume reduction at a desired rate and (d) said catheter does not occlude the bronchii leading to said target lung area.

22. A method for reducing the volume of a lung area, the method comprising:
  a. Catheterizing said lung area with an indwelling catheter for an extended period of at least 72 hours; wherein said catheter is anchored in the bronchus without occluding the bronchus to remain in place for said period automatically without trapping organisms in the area and without requiring being held in place by a person and without requiring continuous observation by a clinician.
  b. Displacing the native gas in said lung area by delivering a Diffusible Low Molecular Weight (DLMW) gas into said area via said catheter and maintaining a patent exhaust pathway through the bronchii leading to said area during the extended period for the escape of the naturally residing native respiratory gas consisting of oxygen, CO2 and N2, and the DLMW gases;
  c. Regulating the pressure of said DLMW gas delivery to maintain a desired pressure in said lung area, said regulation designed to create a gradient of higher gas pressure in said lung area compared to gas pressure in neighboring lung areas, said gradient sufficient to inhibit infusion of gases into said lung area from neighboring lung areas through interconnecting collateral channels, and to force effusion of said delivered DLMW gas out of said area, said effusion sufficient to effect at least partial volume reduction of said lung area.

23. A method as in claim 22 wherein the amplitude of said gradient is reduced over time to facilitate at least partial deflation of said lung area.

24. A method as in claim 22 wherein said DLMW gas delivery pressure regulation is regulated to create a pressure in said lung area that is at least temporarily 2-20 cwp greater than the neighboring area gas pressure, to achieve the desired amount of volume reduction.

25. A method as in claim 22 wherein said catheter is placed through the user's upper airway.

26. A method as in claim 22 wherein the distal tip of said catheter is placed in a bronchus at a lung depth between the lobar and subsegmental bronchii, including the lobar and subsegmental bronchii.

27. A method as in claim 22 wherein said catheter intermittently occludes the bronchus directly proximal to and leading to said lung area to facilitate regulating the flow of DLMW gas out of the lung area into neighboring lung areas through collateral channels interconnecting said lung area with said neighboring lung areas.

28. A method as in claim 22 wherein said DLMW gas is delivered at a variable pressure amplitude.

29. A method as in claim 22 wherein said DLMW gas is delivered non-continuously in an oscillatory flow pattern.

30. A method as in claim 22 wherein the gas in said lung area exhausts out of the lung area passively around the outside of said catheter and through a lumen inside said catheter and through collateral channels interconnecting said lung area with neighboring lung areas.

31. A method as in claim 22 wherein said gas flow in the proximal direction is actively assisted by the application of vacuum to said area.

32. A method as in claim 22 wherein the gas in said lung area exhausts out of said lung area with the assistance of the application of vacuum to neighboring lung areas, thereby augmenting said gas exhaust from said lung area into said neighboring lung areas through collateral channels interconnecting said lung area with said neighboring lung areas.

33. A method as in claim 22 wherein gas flow in the proximal direction out of said lung area and said DLMW gas delivery is conducted through at least one lumen in said catheter.

34. A method as in claim 22 wherein the catheter intermittently partially obstructs the bronchus proximal to and feeding said lung area to facilitate said delivery of DLMW gas and displacement of resultant mixed gases.

35. A method as in claim 22 wherein said DLMW gas possesses greater diffusivity and lower molecular weight than that of said native gas, said molecular weight 2-20 atomic mass units to achieve the desired volume reduction and diffusivity of at least $10^{-4}$ cm2/sec.

36. A method as in claim 22 wherein said DLMW gas delivery is performed for at least a subchronic period of over 7 days.

37. A method as in claim 22 wherein after said volume reduction of said area, said area is maintained at the reduced volume by use of tissue expansion restraining device.

38. A method as in claim 1 wherein said targeted lung area is pre-conditioned with a substance to make it less susceptible to infection, the substance comprising antibiotics.

39. A method as in claim 1 wherein said targeted lung area is pre-conditioned with a substance to make it more susceptible to deflation the substance selected from the group of mucolytic agents, bronchodilators, surface tension modifiers, and tissue diffusivity modifiers.

40. A method as in claim 1 wherein said catheter is placed through an ostomy in the crico-tracheal structure.

41. A method as in claim 1 wherein multiple lung areas are treated sequentially.

42. A method as in claim 1 wherein said catheter is positioned using fluoroscopy visual assistance.

43. A method as in claim 1 wherein said catheter is positioned with the assistance of a guiding element.

44. A method as in claim 1 wherein said DLMW gas is delivered at a variable pressure amplitude.

45. A method as in claim 1 wherein said DLMW gas is delivered using an oscillatory flow pattern synchronized with the patient's breath cycle.

46. A method as in claim 1 wherein said DLMW gas delivery is performed as an extended sub-chronic procedure consisting of one to 14 days.

47. A method as in claim 1 wherein said DLMW gas delivery is performed as a chronic procedure consisting of 14 to 90 days.

48. An apparatus for reducing the residual volume of a target lung area and increasing the volume of a neighboring lung area, the apparatus comprising:
   a. a supply of diffusible low molecular weight (DLMW) gas, the gas comprising a molecular weight of 2-20 atomic mass units and a diffusivity of at least $10^{-4}$ cm2/sec;
   b. a catheter connected at one end to the supply of DLMW and the opposite distal end placed in a bronchus leading to said target lung area, wherein the catheter comprises a non-occlusive anchoring means which maintains a patent airway and which permits extended placement of the catheter distal end without movement and without requiring continuous supervision or position maintenance from a person;
   c. a pressure regulator control means to control the DLMW pressure in the target area to a desired pressure higher than the pressure of the neighboring lung areas.

* * * * *